United States Patent [19]
Dunstan et al.

[11] Patent Number: 5,614,496
[45] Date of Patent: Mar. 25, 1997

[54] USE OF FIBROBLAST GROWTH FACTORS TO STIMULATE BONE GROWTH

[75] Inventors: Colin R. Dunstan; Elzbieta Izbicka; Gregory R. Mundy, all of San Antonio, Tex.; Wilson Burgess, Gaithersburg, Md.; Michael C. Jaye, Glenside, Pa.

[73] Assignees: OsteoSA Inc., San Antonio, Tex.; Rhone-Poulenc Rorer Pharmaceuticals Inc., Collegeville, Pa.

[21] Appl. No.: 458,634

[22] Filed: Jun. 2, 1995

Related U.S. Application Data

[63] Continuation of Ser. No. 207,985, Mar. 8, 1994, abandoned.
[51] Int. Cl.$^6$ .......................... A61K 38/18; A61K 38/16; C07K 14/475; C07K 14/50
[52] U.S. Cl. ................... 514/12; 514/21; 514/25; 530/351; 530/840; 424/85.1
[58] Field of Search .................... 530/351, 840; 514/12, 21; 424/85.1

[56] References Cited

U.S. PATENT DOCUMENTS

| | | | |
|---|---|---|---|
| 4,642,120 | 2/1987 | Nevo et al. | 623/16 |
| 4,868,113 | 9/1989 | Jaye et al. | 435/69.4 |
| 5,077,049 | 12/1991 | Dunn et al. | 424/426 |

OTHER PUBLICATIONS

Simmons et al. "Effects of Acid & Basic Fibroblast Growth Factor & Heparin on Resorption of Cultered Fetal Rat Long Bones" J Bone Min Des. 6(12) 1301–1305 1991.

Jingushi et al. "Acidic Fibroblast Growth Factor (aFGF) Injection Stimulate Cartilage Enlargement & Inhibits Cartilage Gene Expression in Rat Fracture Healing" J. Ortho. Res. 8(3) 364–371 1990.

Mayo et al. "Morphogenic Effects of Acidic Fibroblast Growth Factor on Mouse Molars" J. Dent. Res. 72 (1 ADR Abstracts) 110 Abstract #55 Feb. 1, 1993.

Aoh "Wheelers Dental Anatomy, Physiology, and Occlusion" 1984. 33–39.

The Journal of Biological Chemistry, vol. 261, No. 27, 12665 (1986), Hauschka, Mavrakos, Iafrati, Doleman, Klagsbrun, Growth Factors in Bone Matrix.

Endocrinology, vol. 123, No. 1, 98 (1988), Globus, Patterson–Bucke, Gospodarowicz, Regulation of Bovine Bone Cell Proliferation by Fibroblast Growth Factor and Transforming Growth Factor.

Growth Factors, vol. 9, 73 (1993), Mayahara, Ito, Nagai, Miyajima, Tsukuda, Taketomi et al., In Vivo Stimulation of Endosteal Bone Formation by Basic Fibroblast Growth Factor in Rats.

J. Clin. Invest., vol. 81, 1572 (1988), Canalis, Centrella, McCarthy, Effects of Basic Fibroblast Growth Factor on Bone Formation in Vitro.

Endocrinology, vol. 125, No. 4, 2118 (1989), McCarthy, Centrella, Canalis, Effects of Fibroblast Growth Factors on Deoxyribonucleic Acid and Collagen Synthesis in Rat Parietal Bone Cells.

FEBS Letters, vol. 250, No. 2, 619 (1989), Noff, Pitaru, Savion, Basic fibroblast growth factor enhances the capacity of bone marrow cells to form bone–like nodules in vitro.

Clinical Orthopaedics and Related Research, No. 263, 30 (1991), Mohan, Baylink, Bone Growth Factors.

(List continued on next page.)

*Primary Examiner*—Mindy Fleisher
*Assistant Examiner*—Nancy J. Degen

[57] ABSTRACT

The present invention provides therapeutic compositions for the prevention and treatment of pathological conditions involving bone and dental tissue. The present invention also provides a method to promote bone repair and/or growth for the treatment of pathological conditions involving bone tissue, for example, osteoporosis, Paget's disease, osteopetrosis, and periodontal disease and fracture repair, and healing of bone defects by administering FGF-1 to an animal or human in need of treatment.

17 Claims, 9 Drawing Sheets

* Different to untreated control p<0.05

OTHER PUBLICATIONS

Journal of Cellular Biochemistry, vol. 50, 392 (1992), Chanoine, Stein, Braverman, Shalhoub, Lian, Huber et al., Acidic Fibroblast Growth Factor Modulates Gene Expression in the Rat Thyroid in Vivo.

Annu. Rev. Med., vol. 42, 17 (1991), Canalis, McCarthy, Centrella, Growth Factors and Cytokines in Bone Cell Metabolism.

J. Endocrinol. Invest., vol. 12, 577 (1989), Canalis, McCarthy, Centrella, Growth factors and the skeletal system.

Calcium Regulation and Bone Metabolism, Elsevier Science, 257 (1990), Mundy, Roodman, Yoneda, Bonewald, Oreffo, Growth regulatory factors and bone cell function.

Acta Orthop. Scand, vol. 65(1), 27 (1994), Wang, Aspenberg, Basic fibroblast growth factor increases allograft incorporation—Bone chmber study in rats.

Adv. Exp. Med. Biol., vol. 324, 101 (1992), Suzuki, Effects of Various Growth Factors on a Chondrocyte Differentitation Model.

J. Periodontol, vol. 63, No. 6,515 (1992), Matsuda, Lin, Kumar, Cho, Genco, Mitogenic, Chemotactic, and Synthetic Responses of Rat Periodontal Ligament Fibroblastic Cells to.

Journal of Bone and Mineral Research, vol. 6, No. 12, 1373 (1991), Hiraki, Inoue, Shigeno, Sanma. Bentz, Rosen et al., Bone Morphogenetic Proteins (BMP-2 and BMP-3) Promote Growth and Expression of the Differentiated Phenotype of.

Blood, vol. 83, No. 4, 907 (1994), Gabrilove, White, Rahman, Wilson, Stem Cell Factor and Basic Fibroblast Growth Factor Are Synergistic in Augmenting Committed Myeloid.

Plastic and Reconstructive Surgery, vol. 88, No. 1, 1 (1991), Eppley, Connolly, Winkelmann, Sadove, Heuvelman, Feder, Free Bone Graft Reconstruction of Irradiated Facial Tissue: Experimental Effects of Basic Fibroblast.

Endocrinology, vol. 130, No. 5, 2675 (1992), Hurley, Kessler, Gronowicz, Raisz, The Interaction of Heparin and Basic Fibroblast Growth Factor on Collagen Synthesis in 21-Day Fetal Rat Calvariae.

Int. J. Dev. Biol., vol. 33, 165 (1989), Partanen, Thesleff, Growth Factors and Tooth Development.

Acta Anat., vol. 145, 265 (1992), Frenkel, Herskovits, Singh, Fibroblast Growth Factor: Effects on Osteogenesis and Chondrogenesis in the Chick Embryo.

Biomaterials, vol. 11, 38 (1990), Frenkel, Grande, Collins, Singh, Fibroblast growth factor in chick osteogenesis.

Anat. Rec., vol. 232, No. 4, 34A (1992), Frenkel, Herskovits, Singh, In vivo effects of fibroblast growth factor (FGF) on osteogenesis in the chick embryo.

J. Bone and Mineral Research, vol. 8 (Supp. 1): S179, 1993, Dunstan, Boyce, Izbicka, Adams, Mundy, Acidic and Basic Fibroblast Growth Factors Promote Bone Growth In Vivo Comparable to that of TGF Beta.

EP 0499242, Feb. 13, 1992, Aug. 19, 1992, Mayahara, Ito, Kato, Stimulation of endosteal bone formation with a cell growth factor.

Toxicology Letters, 64/65: 329–338, 1992, Mazue, Bertolero, Garofano, Brughera, Carminati, Experience with the preclinical assessment of basic fibroblast growth factor (bFGF).

Acta Orthop Scand, 62(5): 481–84, 1991, Aspenberg, Thorngren, Lohmander, Dose-dependent stimulation of bone induction by basic fibroblast growth factor in rats.

Endocrinology, 135(2): 774–81, 1994, Kawaguchi, Kurokawa, Hanada, Hiyama, Tamura et al., Stimulation of Fracture Repair by Recombinant Human Basic Fibroblast Growth Factor in Normal and.

Acta Orthop Scand, 60(4): 473–76, 1989, Aspenberg, Lohmander, Fibroblast growth factor stimulates bone formation.

Nippon. Seikeigeka. Gakkai. Zasshi. 64:824–834 (1990), Hatori, Journal: Nippon. Seikeigeka. Gakkai. Zasshi. 64:824–834 (1990).

WO92/09301, Nov. 27, 1991, Jun. 11, 1992, Nunez, Drohan, Burgess, Tissue Sealant and Growth Factor Containing Compositions That Promote.

US 5,348,941, Apr. 1, 1992, Sep. 20, 1994, Middaugh, Tasi, Wolkin, Stabilizers for Fibroblast Growth Factors.

* Different to OVX-PBS p<0.01, # different to SHAM-PBS P<0.01

USE OF FIBROBLAST GROWTH FACTORS TO STIMULATE BONE GROWTH

This is a continuation of application Ser. No. 08/207,985 filed on Mar. 8, 1994, now abandoned.

BACKGROUND OF THE INVENTION

1. Field of the Invention

The present invention relates to the use of fibroblast growth factors as therapeutic agents for the prevention and treatment of pathological conditions involving bone tissue, for example, osteoporosis, Paget's disease, osteopetrosis, and periodontal disease and fracture repair, and healing of bone defects.

2. Background of the Invention

Living bone tissue is continuously being replenished by the processes of resorption and deposition of bone matrix and minerals. This temporally and spatially coupled process, termed bone remodeling, is accomplished largely by two cell populations, the osteoblasts and osteoblasts. The remodeling process is initiated when osteoblasts are recruited from the bone marrow or the circulation to the bone surface and remove a disk-shaped packet of bone. The bone matrix and mineral is subsequently replaced by a team of osteoblasts recruited to the resorbed bone surface from the bone marrow. Among the pathological conditions associated with abnormal bone cell function is osteoporosis, a diseased characterized by reduced amounts of bone (osteopenia) and increased bone fragility. These changes can be the result of increased recruitment and activity of osteoblasts, often in combination with reduced recruitment or activity of osteoblasts. It is believed that the development of excess or deficient populations of osteoblasts or osteoblasts may result from a corresponding lack or excess of specific protein factors called cytokines.

Cytokines have been identified by their biological characteristics and their unique amino acid sequences. Each cytokine presents a unique spectrum of characteristics that distinguish it from other cytokines. In general, the cytokines stimulate the growth and/or differentiation of specific types of cells. Some cytoines can also target cancerous cells for destruction. Examples of cytokines include granulocyte-colony-stimulating factor (G-CSF), granulocyte-macrophage CSF (GM-CSF), macrophage CSF (M-CSF), interleukin-1 beta, interleukin-3, interleukin-6, interferon-gamma, tumor necrosis factor, lymphotoxin, leukemia inhibitory factor, fibroblast growth factors, transforming growth factor-alpha and transforming growth factor-beta.

Many of the known cytokines stimulate or inhibit blood cells. Several growth regulatory cytokines, such as M-CSF, transforming growth factor alpha, interleukin-1 and tumor necrosis factor, have been shown to stimulate marrow mononuclear cell proliferation. Although cytokines such as interleukin-1 (IL-1), tumor necrosis factor (TNF) and interleukin-6 (IL-6) may influence osteoblast formation and differentiation (Mundy (1990) Trends Endo. Metab. 1:307–311), these factors are not specific osteoblast growth regulatory factors.

Although there is much information available on the factors that influence the breakdown and resorption of bone, information is more limited on factors that can actually stimulate the formation of new bone. Bone itself contains factors that have the capacity for stimulating the growth and/or differentiation of bone cells. Thus, extracts of bone tissue contain not only structural proteins that are responsible for maintaining the structural integrity of bone, but also biologically active bone growth factors that stimulate bone cells to proliferate. Among the growth factors found in bone that are known to stimulate proliferation of bone cells are transforming growth factor $\beta$, the insulin-like growth factors (insulin-like growth factor I and insulin-like growth factor II), basic fibroblast growth factor (bFGF) and bone morphogenetic proteins (BMPs). These factors also cause proliferation of non-bone cell types.

The fibroblast growth factor (FGF) family is comprised of at least 9 structurally related proteins (FGFs 1–9), whose best known members are acidic FGF (aFGF; FGF-1) and basic FGF (bFGF; FGF-2). Members of this family stimulate mitogenesis in most cells derived from the mesoderm and neuroectoderm and influence other biological processes, including anglogenesis, neurite extension, neuronal survival, and myoblast differentiation. In general, FGFs have a high affinity for heparin (prior to resolution of their nomenclature, some FGFs were referred to as heparin-binding growth factors –1, –2, etc.), and many, but not all, are mitogens for fibroblasts. The members of the FGF family possess roughly 25–55% amino acid sequence identity within a core sequence and some FGFs possess significant extensions, either C-terminal, N-terminal, or both, outside of this core sequence. This structural homology suggests that the 9 different genes encoding known FGFs may be derived from a common, ancestral gene.

In addition to the 9 known members of the FGF family, additional complexity results from the generation of several molecular forms of FGF from a single gene. For example, the primary translation product of aFGF (FGF-1) consists of 155 residues. However, the longest form of FGF-1 found in a natural source (e.g., bovine brain) consists of 154 residues. This 154 residue form of FGF-1 lacks the NH2-terminal methionine of the 155 residue form and has an acetylated amino terminus. Proteolytic processing in vivo or during purification generates smaller active forms of FGF-1 in which either the amino-terminal 15 (des 1-15) or 21 (des 1-21) amino acids are deleted. As defined herein, FGF-1 refers to the 154 residue form of FGF-1 and shorter, biologically active forms thereof, such as the above described forms deleted of the amino-terminal 15 (des 1-15) or 21 (des 1-21) amino acids. Historically, the 154 residue form of FGF-1 was termed $\beta$-endothelial cell growth factor ($\beta$-ECGF), the des 1-15 form was termed aFGF, and the des 1-21 form was termed $\alpha$-ECGF. Prior to standardization of the terminology for this group of growth factors, several additional terms were also applied to the same protein, including eye derived growth factor and heparin binding growth factor 1. Similar forms of bFGF (FGF-2) have also been described. In addition to cleaved forms, extended forms of bFGF have also been described, resulting from initiation of translation at several different GTG codons located upstream of the ATG translation initiation codon which generates the 155 residue form of bFGF. All of these alternative forms of the FGFs contain the core region of structural homology which defines the FGF family.

Reported Developments

An osteogenic role for bFGF was suggested based on in vitro studies (Hauschka et al., J. Biol. Chem 261:12665–12674, 1986; Globus et al., Endocrinology 123:98–105, 1988; Canalis et al., J. Clin. Invest. 81:1572–1577, 1988; McCarthy et al., Endocrinology 125:2118–2126, 1989; Noff et al., FEBS Lett., 250:619–621, 1989). However, there has been only one report of in vivo administration of bFGF (Mayahara et al., Growth Factors 9:73–80, 1993). Intravenous administration of human bFGF to rats demonstrated only endosteal new bone formation. No increase in periosteal bone formation was evidenced. Similar systemic osteogenic potential was seen after intravenous administration of human aFGF.

SUMMARY OF THE INVENTION

The present invention a method for treating patients suffering from pathological conditions in which bone mass is inadequate or in repairing defects in bone or dental tissue comprising the administration thereto of pharmaceutical compositions comprising certain fibroblast growth factors in an amount which stimulates the proliferation and/or differentiation of osteoblasts and/or precursors to promote bone anabolism. Preferably the FGFs are applied locally to stimulate periosteal bone formation. Alternatively, systemic application of FGF-1 is preferable for promotion of endosteal bone formation. The fibroblast growth factors preferred in the practice of the present invention are FGF-1 and FGF-2, and, most preferably, full-length FGF-1 (ECGF β) and FGF des 1-21 (ECGF α).

Other and further objects, features and advantages will be apparent from the following description of the preferred embodiments of the invention given for the purpose of disclosure when taken in conjunction with the following drawings.

DESCRIPTION OF THE PREFERRED EMBODIMENTS

Figure 1:
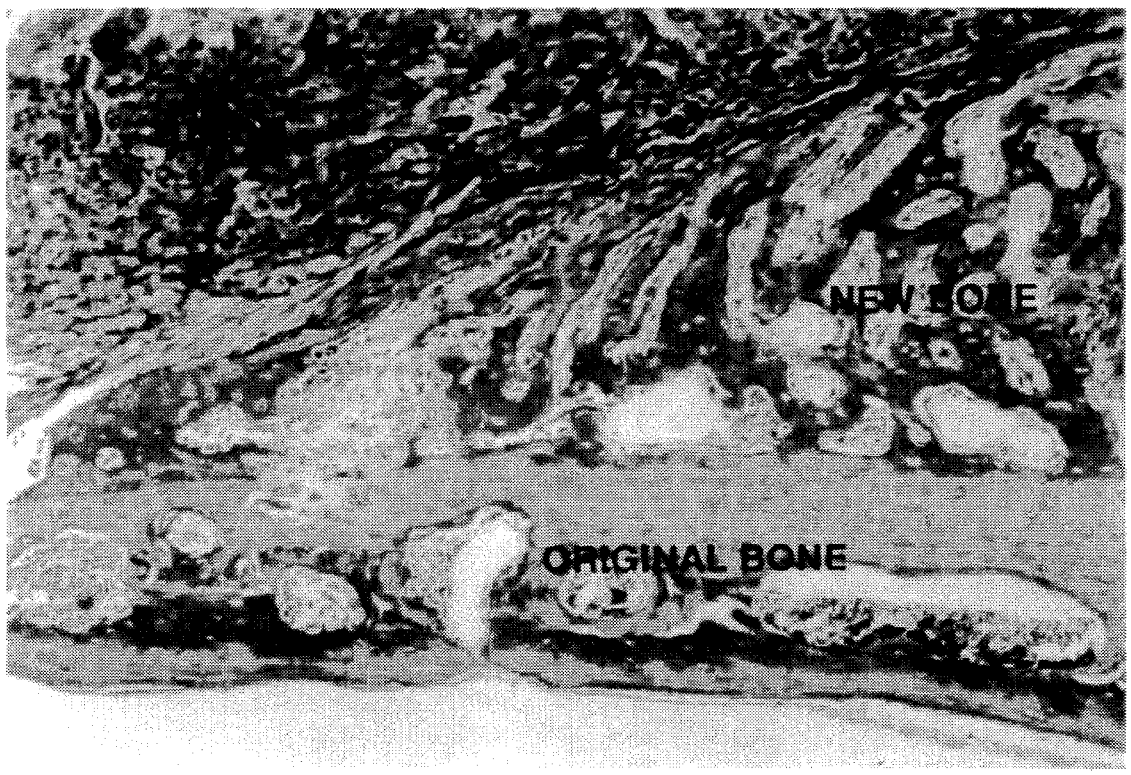
FIG. 1 is a photomicrograph demonstrating new bone growth in the calvaria of the nude mouse adjacent to WISH tumor cells.

A preferred aspect of the present invention provides a method for stimulating bone formation, preferably, periosteal bone formation, useful in treatment of pathological conditions in which bone mass is inadequate or in repairing defects in bone and dental tissue. In one embodiment the present method and compositions are particularly useful in enhancing periosteal bone formation following local application to promote a net increase in cortical bone. The invention encompasses the use of naturally occurring fibroblast growth factors in partially purified, as well as substantially homogeneous, form, as well as synthetically or recombinantly produced fibroblast growth factors, biologically active fragments thereof, and pharmaceutically acceptable salts and derivatives thereof.

Definitions

"Substantially purified" is used herein as "substantially homogeneous" which is defined as a proteinaceous material which is substantially free of compounds normally associated with it in its natural state (e.g., other proteins or peptides, carbohydrates, lipids). Most preferably, it means a polypeptide, which may be glycosylated or nonoglycosylated, which is characterized by a single molecular weight and/or multiple set of molecular weights, chromatographic response and elution profiles, amino acid composition and sequence and biological activity. "Substantially purified" is not meant to exclude artificial or synthetic mixtures with other compounds. The term is also not meant to exclude the presence of impurities which do not interfere with biological activity, and which may be present, for example, due to incomplete purification or compounding with a pharmaceutically acceptable preparation.

The term "animal" includes, but is not limited to, mammals, such as dogs, cats, horses, cows, pigs, rats, mice, simians, and humans.

The term "biologically active polypeptide" means naturally occurring polypeptide per se, as well as biologically active analogues thereof, including synthetically produced polypeptides and analogues thereof, as well as natural and pharmaceutically acceptable salts and pharmaceutically acceptable derivatives thereof.

The term biologically active polypeptide also encompasses biologically active fragments thereof, as well as biologically active sequence analogues thereof. Different forms may exist in nature. These variations may be characterized by differences in the nucleotide sequence of the structural gene coding for proteins of identical biological function.

The term "biologically active sequence analogue" includes naturally and non-naturally occurring analogues having single or multiple amino acid substitutions, deletions, additions, or replacements. All such allelic variations, modifications, and analogues resulting in derivatives which retain one or more of the native biologically active properties are included within the scope of this invention.

The term "FGF-1" encompasses the 154 residue form of FGF-1 acidic growth factors (also known as ECGF β), the des 1-15 form and the des 1-21 form (also known as ECGF α). FGF-1 may be prepared by methods known in the art. Preferably, the FGF-1 used in the present invention is prepared by recombinant technology, such as disclosed in U.S. Pat. No. 4,868,113, which patent is incorporated herein by reference.

To purify the polypeptides useful in practicing the present invention, either from natural sources or after recombinant production, chromatographic procedures may be carried out, for example in a narrow bore column containing a fine particle resin under increased pressure to enhance the effectiveness of separation, i.e., by high pressure liquid chromatography.

Concentration and salt removal are commonly used steps in certain chromatographic or separation techniques employed in the invention.

Salt removal is generally necessary if ion exchange or other techniques which depend on ionic strength are employed. Salt removal may be performed by, for example, dialysis or gel filtration or by control pore glass (CPG) chromatography.

A number of gel filtration and concentration techniques are also used. Certain commercially available materials are especially useful. Sephacryl, Sephadex, and Bio-Gel are examples of gel filtration media commonly used to isolate and purify proteins and characterize their physical properties.

The invention encompasses methods of using fibroblast growth factors, preferably FGF-1, bFGF and new forms of basic FGF isolated from WISH cells, in treatment of bone diseases associated with reduced skeletal mass or defective or deficient bone formation. Acidic FGF and basic FGF stimulate the growth of human cells with the osteoblast phenotype and their precursors. In one embodiment, the present invention provides a method for the treatment of human and animal disorders characterized by an abnormally reduced level of osteoblastic cell proliferation.

Administration of the fibroblast growth factors to effect the therapeutic objectives of the present invention may be by local, parenteral, intravenous, intramuscular, subcutaneous, rectal or any other suitable means. The dosage administered may be dependent upon the age, weight, kind of concurrent treatment, if any, and nature of the bone pathology being treated.

The therapeutic method of the present invention may be employed by administering fibroblast growth factors in such forms as liquid solutions, suspensions, elixirs, or sterile liquid forms. Suitable carriers include diluents or fillers, sterile aqueous media and various non-toxic organic solvents. The compositions may be formulated in the form of powders, aqueous suspensions, or solutions, injectable solutions, elixirs, syrups and the like and may contain one or more stabilizing agents such as human serum albumin, sugar (including, but not limited to, glycosoaminoglycans such as heparin or heparin fragments) or amino acid, antibacterial, and preserving agents in order to provide a pharmaceutically acceptable preparation. Any inert carrier is preferably used, such as saline, or phosphate-buffered saline, or any such carrier in which the factors used in the method of the present invention have suitable solubility properties. Carriers such as devitalized bone powder, hydroxyapatite or fibrin sealant may also be used to practice the present invention.

The particular carrier and the ratio of active compound to carrier are determined by the solubility and chemical properties of the proteinaceous factors, the particular mode of administration and standard pharmaceutical practice. For parenteral administration, solutions or suspensions of these factors in aqueous alcoholic media or in sesame or peanut oil or aqueous solutions of the soluble pharmaceutically acceptable salts can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of about 0.1 mg/kg to about 500 mg/kg, preferably about 1 mg/kg to about 250 mg/kg, and most preferably about 5 mg/kg to about 100 mg/kg of body weight in injectable form; such may, of course, be given in divided doses. With other forms of administration equivalent or adjusted doses will be administered depending on the route of administration.

The following examples describe the isolation, purification and measurement of biological activity of the fibroblast growth factors and their use as therapeutic agents for the prevention and treatment of pathological conditions of bone defects, injuries and are not intended to be limiting unless so expressly stated.

EXAMPLE 1

Assay of Proliferative Effects of Fibro blast Growth Factors on Osteosarcoma Cells and Osteoblast Bone Cells The proliferative effects of fibroblast growth factors on MG-63 human osteosarcoma cells and MC3T3 bone cells is assessed by measuring the incorporation of tritiated thymidine into cellular DNA.

MG-63 human osteosarcoma cells, obtained from the American Type Culture Collection (Rockville, Md.), are cultured in Eagle's minimum essential medium (EMEM) supplemented with 10% fetal bovine serum (FBS). MC-3T3EI mouse osteoblasts, provided by Dr. T. Suda (Showa University, Tokyo), are cultured in alpha modification of Eagle's medium ($\alpha$MEM) supplemented with 10% FBS. All cultures are maintained at 37° C., in a humidified atmosphere of 5% $CO_2$ in air.

MG-63 and MC3T3 cells are seeded at $5 \times 10^3$ cells/100 $\mu$l/well in 96 well plates in EMEM or $\alpha$MEM, respectively, supplemented with 10% FBS. After incubation for approximately 18–24 hours, the cells are washed with 200 $\mu$l/well of phosphate buffered saline (PBS), re-fed with 50 $\mu$l/well of serum free 0.1% BSA in EMEM or $\alpha$MEM and 50 $\mu$l/well of a sample containing growth factor activity diluted in 0.1% BSA in DMEM/F12 is added. Baseline controls (50 $\mu$l/well of 0.1% BSA in DMEM/F12 50/50) as well as positive controls (50 $\mu$l/well of 20% FBS in DMEM/F 12 50/50) are run in each plate in parallel with the test sample. About 44 hours after the addition of the sample and controls, the cells are pulsed with 1 $\mu$Ci/well of [methyl $^3$H] thymidine for 4 hours. After 4 hours, the cells are collected and rinsed on filter paper discs using a PHD cell harvester (Cambridge Technology, Watertown, Ma.). The radioactivity retained by the filters is measured as cpm using a liquid scintillation counter (Beckman, Fullerton, Calif.).

The proliferative activity of each sample (run in duplicate) is expressed as percentage of the stimulation of incorporation of $^3$H thymidine caused by the positive control, by using the formula:

$$\frac{cpm \text{ sample} - cpm \text{ baseline control}}{cpm \text{ positive control} - cpm \text{ baseline control}} \times 100$$

EXAMPLE 2

Purification of the Biological Activity of Extended bFGF from WISH Cells

A. Growth of Tumor In Vivo

Human amniotic tumor cells ($2 \times 10^7$) were injected into the right hind limb area adjacent to the femoral shaft of fourteen 4 week old male nude mice. Solid tumors were isolated from the animals after 3–5 weeks. At this time, there was evidence of new bone growth as assessed radiologically and histologically. In 10 mice, tumor was closely adhered to the bone surface and in each of these there was evidence of new bone growth. New bone growth was easily recognized by its woven, rather than lamellar, structure, and was extensive on periosteal bone surfaces adjacent to the tumor mass. Solid tumor was removed from the bone and immediately frozen in liquid nitrogen for subsequent protein purification. For quantitative histomorphometry, the cells ($1 \times 10^7$ cells/ 0.2 ml PBS) were injected subcutaneously over the calvariae of nude mice (n=8). The mice were sacrificed after two weeks. In six mice, tumor closely adhered to the bone surface. Histological methods for preparing the bone samples were as described in Example 3 below. There was extensive new bone formation over the calvaria of these mice (FIG. 1) and the cross-sectional area of the calvarial bone was increased 96±37 (S.D.) %.

B. Isolation and Purification of Extended bFGF

Twenty-five grams of solid tumor tissue isolated from femora of tumor-bearing mice were pulverized in liquid nitrogen and extracted by stirring at 4° C. for 72 hours in 125 ml of extraction buffer containing 10 mM EDTA, 50 mM Tris-HCl pH 7.0, 1.5M NaCl, 25 mM benzamidine, 1 µg/ml each of leupeptin and aprotinin, and 1 mM PMSF (dissolved in 100% isopropanol), adjusted to a final pH of 7.0. After 72 hours, the extract was centrifuged at 6000 rpm for 20 min at 4° C. The supernatant was removed and frozen at −70° C.

A second extraction of the insoluble precipitate from the initial extraction was performed in the same buffer by adding 250 ml of fresh extraction buffer to the pellet and stirring the mixture at 4° C. for another 24 hours. After this period, the extract was centrifuged at 6000 rpm for 20 min at 4° C. Supernatants from the first and second extractions were combined and centrifuged at high speed at 15,000 g for 1 hr at 4° C. The supernatant was removed, and dialyzed against 10 mM Tris-HCl, 0.1M NaCl, pH 7.0. Protein concentration was determined by the absorbance at 280 and 260 nm.

A 4.8×30 cm column was packed with heparin Sepharose CL-6B and equilibrated with a buffer containing 0.1M NaCl, 10 mM Tris-HCl, pH 7. The final extract (approx. 200 ml) was applied to the column. The column was washed with the same buffer and eluted with a linear gradient from 0.4–3.0M NaCl. Twelve ml fractions were collected. Aliquots of each fraction were assayed in the MG-63 and MC3T3 proliferative assays described in Example 1. Fractions containing MG-63 proliferative activity eluted at 1.5M NaCl and were rechromatographed on heparin-Sepharose under the same conditions. Fractions containing MG-63 proliferative activity eluted at 1.8M NaCl. These fractions (34–44) were pooled, adjusted to 0.05% CHAPS ((3-[(3-cholamidopropyl)-dimethylammonio]-1-propane-sulfonate; a mild zwitterionic detergent) and dialyzed against 50 mM sodium phosphate pH 6.0, 0.05% CHAPS. The dialysate was chromatographed on a MonoS FPLC column in a gradient from 0 to 1.0M NaCl in 50 mM sodium phosphate pH 6.0, 0.05% CHAPS. Factions of 0.8 mls were collected. The MG-63 positive fractions (26–32) were pooled and injected into a C4 or C18 HPLC column and chromatographed in a gradient from 7% to 63% acetonitrile in 0.1% TFA. For biological activity measurements, 10% of the material was run in a C18 RPHPLC column and the fractions were collected in a neutralizing solution (24 mM ammonium bicarbonate pH 8, 0.1% BSA, 2 µg/ml heparin and 0.01% CHAPS). Protein eluting at 37% acetonitrile was subjected to SDS-PAGE (15% gel) and transblotted to a nitrocellulose membrane (0.45 µm, Schleicher & Schuell, Keene, N.H.). Amino acid sequence was obtained by automated Edman degradation using an Applied Biosystems Model 477A protein sequencer equipped with an online Model 120A PTH Analyzer.

The amino acid sequence of the polypeptide isolated and purified from the WISH cells is similar, but not identical, to the amino acid sequence of bFGF. The novel sequence appears to define a heretofore unknown extended form of basic FGF, having the additional amino acid sequence Gly-Ser-Arg-Pro-Gly-Ala-Gly-Thr (SEQ ID NO: 1) extending the N-terminal end Met-Ala-Ala-Gly-Ser-Ile-Thr (SEQ ID NO: 2) of the known 18 kD form of bFGF.

EXAMPLE 3

In Vivo Assay of Effects of Polypeptides on Bone Growth

The effects of the polypeptide factors on bone growth were tested in male ICR Swiss white mice, aged 4–6 weeks and weighing 13–26 gms using 4–5 mice per group. The polypeptide or a control vehicle was injected into the subcutaneous tissue over the right calvarium of normal mice. Among the polypeptides tested were the crude extract from WISH tumors containing the extended form of bFGF isolated as described in Example 2, basic FGF and FGF-1 which comprises acidic FGF. These test proteins were injected either alone or together with heparin.

Unless otherwise specified, the control vehicle was PBS supplemented with 1% BSA. Heparin was administered at a dose of 50 units/ml. The animals were sacrificed on day 14 and bone growth measured by histomorphometry.

Bone samples for quantitation were cleaned from adjacent tissues and fixed in 10% buffered formalin for 24–48 hours, decalcified in 14% EDTA for 1–3 weeks, processed through graded alcohols and embedded in paraffin wax. Three µm sections of the calvaria and femurs were prepared. Representative sections were selected for histomorphometric assessment of the effects of the tumors, tumor extracts or fibroblast growth factors comprising acidic or basic FGF on bone formation and bone resorption. Sections were measured by using a camera lucida attachment to directly trace the microscopic image onto a digitizing plate. Bone changes were measured on sections collected 200 µm apart, over 4 adjacent 1×1 mm fields on both the injected and noninjected sides of the calvaria. New bone was identified by its woven, rather than lamellar structure, and osteoblasts and osteoblasts were identified by their distinctive morphology. Histomorphometry software (Osteomeasure, Osteometrix, Inc., Atlanta) was used to process digitizer input to determine cell counts and feature areas or perimeters.

To identify whether mineralization of newly formed bone occurred normally, calvaria bone samples were also taken after animals were administered two doses of tetracycline (25 mg/kg i.p.). Tetracycline is deposited at the sites of active bone formation and functions as a timed-tissue marker to calculate bone formation rates and assess mineralization. These bone samples were fixed as described above, processed through graded alcohols and embedded undecalcified in a methacrylate based plastic to preserve the tetracycline labels. Sections were cut at five µm intervals and were assessed for the degree of mineralization and for tetracycline uptake. The results of these experiments are described in Example 4.

EXAMPLE 4

In Vivo Assay of Effects Fibroblast Growth Factors on Bone Growth

The effects of the polypeptide factors on bone growth were tested in male ICR Swiss white mice, aged 4–6 weeks and weighing 13–26 gms using 4–5 mice per group. The polypeptide or a control vehicle is injected into the subcutaneous tissue over the calvarium of normal mice. Among the polypeptides tested were the extended bFGF isolated from WISH cells as described in Example 2, full length (155 residue) fibroblast growth factor-1 and basic FGF. These test proteins were injected either alone or together with heparin.

In one experiment, the control vehicle was PBS supplemented with 1% BSA. Heparin was administered at a dose of 50 units/ml. Table 1 summarizes the results of four, when included, injections per day for 3 days of either vehicle alone, vehicle supplemented with heparin, 5 μg of IGF1 or IGF2, 1 μg of aFGF[1] together with heparin, and crude extract from the first ("WISH crude") and second ("WISH partially purified") extractions of WISH cells. The animals were sacrificed on day 14 and bone growth measured by histomorphometry.

[1] All experiments utilizing aFGF or FGF-1 herein utilize the 154 amino acid form of the protein, also termed ECGF-β. The terms aFGF and FGF-1 are used interchangeably throughout this application and in the Figures attached hereto.

clocycline (25 mg/Kg) was given IP on days 4, 8 and 12 to calculate bone formation rates and assess mineralization.

Figure 2:
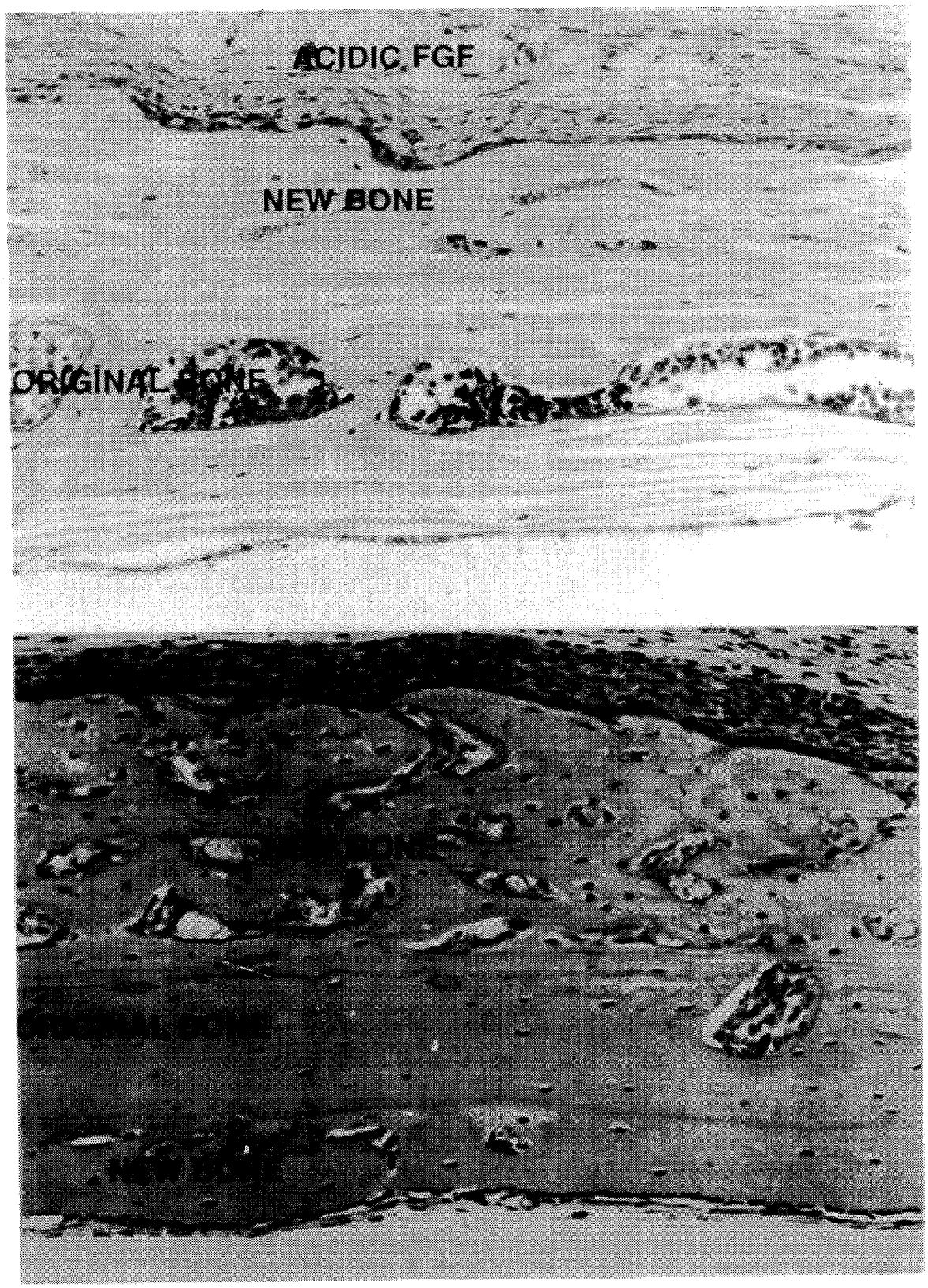
FIG. 2 is a photomicrograph demonstrating new periosteal bone growth in the mouse calvaria after administration of acidic FGF (panel A) and basic FGF (panel B).

The mice were sacrificed on day 14 and the posterior half of the calvaria was decalcified and paraffin embedded. The anterior half of the calvaria, the tibial and femoral metaphysis and lumbar vertebra were embedded undecalcified in plastic. Mice receiving aFGF and bFGF showed extensive new bone formation over the upper surface of the calvaria (FIG. 2). No effects were detected in the femoral metaphysis TABLE 1[b]

|  | PBS + BSA<br>n = 5 | PBS + BSA + Heparin<br>n = 5 | IGF-1<br>5 μg/inj<br>n = 5 | IGF-2<br>5 μg/inj<br>n = 5 | aFGF + hep<br>1 μg/inj<br>n = 5 | WISH crude<br>n = 5 | WISH pp<br>n = 4 |
|---|---|---|---|---|---|---|---|
| Max. New Bone Width % | 12.3 ± 1.8 | 14.4 ± 4.1 | 19.9 ± 2.6 | 17.4 ± 1.4 | 55.1 ± 9.4[a] | 13.4 ± 1.5 | 13.7 ± 1.6 |
| New Bone (% total bone) | 1.8 ± 0.5 | 2.6 ± 0.8 | 3.2 ± 0.6 | 3.3 ± 0.8 | 20.3 ± 3.5[a] | 2.2 ± 0.6 | 2.9 ± 0.7 |
| Osteoblasts (% periosteal surface) | 20.7 ± 7.0 | 25.3 ± 4.5 | 20.4 ± 2.1 | 30.2 ± 1.5 | 93.0 ± 3.5[a] | 29.2 ± 6.9 | 34.3 ± 6.9 |
| Osteoclasts/mm$^2$ Bone Area | 7.9 ± 1.8 | 6.4 ± 2.2 | 9.7 ± 0.9 | 8.8 ± 1.0 | 10.5 ± 2.6 | 8.1 ± 2.8 | 8.5 ± 2.0 |
| Marrow Area (% total) | 6.8 ± 2.2 | 4.5 ± 1.7 | 6.0 ± 1.3 | 6.6 ± 1.6 | 4.9 ± 1.2 | 6.4 ± 1.3 | 7.2 ± 0.9 |

[a]Statistically significant as compared to PBS + BSA + heparin, p < 0.001 (Bonferroni t-test).
[b]Data expressed as mean ± S.E.

As demonstrated on Table 1, FGF-1, injected with heparin over the calvaria of mice, was able to induce new periosteal bone formation. In this experiment no other treatments produced significant new bone formation relative to the control. The proliferative activity of injected WISH extracts, administered in the absence of heparin, was probably only equivalent to 10–100 ng of FGF. There was no evidence of increased bone resorption in any of the treated groups.

In order to further examine the effect of FGF's on bone growth and the effect of heparin on the stimulation of bone growth, 1 μg of FGF-1 or bFGF in the presence of absence of heparin, in a volume of 10 μl, were administered to Swiss ICR white male mice aged 4–6 weeks (five for each treatment group) by injection over the calvaria 4 times per day for 3 days. The control vehicle was 0.1% BSA in PBS. Heparin was administered at a dose of 50 units/ml. Demeor the vertebra. The new bone formed in the more recently formed superficial layers. It was well mineralized and showed diffuse uptake of the demeclocycline labels, typical of woven bone.

TABLE 2**

|  | Total Bone Area (mm$^2$) | Max. New Bone Width (% orig.) | % New Periosteal Bone | % New Endosteal Bone | Osteoblasts (% periosteal surface) | Osteoclasts/mm$^2$ Bone Area | % Marrow Space in Original Bone |
|---|---|---|---|---|---|---|---|
| PBS | 0.76 ± .06 | 26 ± 3 | 3.6 ± 0.5 | 0 | 33 ± 5 | 20.3 ± 3.3 | 7.1 ± 2.1 |
| PBS + heparin | 0.79 ± .02 | 26 ± 2 | 4.0 ± 0.8 | 0 | 35 ± 10 | 14.8 ± 6.2 | 6.6 ± 1.6 |
| aFGF | 0.98 ± .05 | 62 ± 10* | 20.4 ± 6.1* | 3.9 ± 1.4 | 71.2 ± 10.3 | 10.7 ± 1.6 | 4.25 ± 1.0 |
| aFGF + heparin | 1.04 ± .02 | 74 ± 5* | 29.1 ± 4.2* | 1.3 ± 0.9 | 76.8 ± 9.7* | 18.7 ± 3.6 | 8.27 ± 2.0 |
| bFGF | 1.26 ± .06 | 122 ± 20* | 59.6 ± 9.3* | 24.2 ± 6.3* | 81.8 ± 10.3* | 19.4 ± 2.2 | 2.97 ± 1.0 |
| bFGF + heparin | 1.12 ± .06 | 118 ± 20* | 46.9 ± 2.7* | 1.1 ± 1.1 | 88.7 ± 4.3* | 33.0 ± 4.4 | 5.62 ± 2.2 |

**Mean ± S.E.
*statistically significant difference as compared to control p < 0.01

Figure 3:
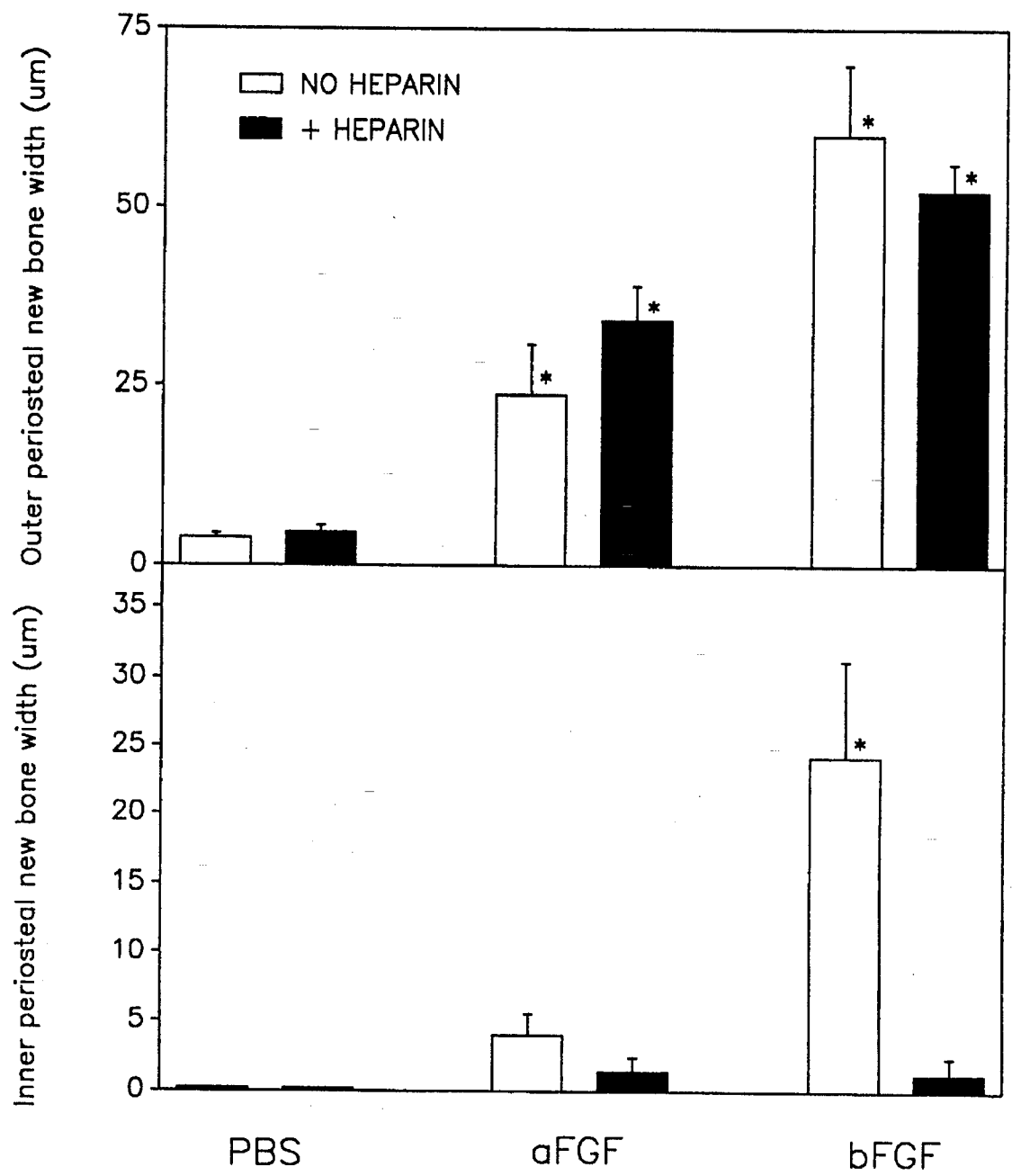
FIG. 3 demonstrates the effects of acidic and basic FGF on calvaria bone growth.

Table 2 and FIG. 3 demonstrate that both aFGF and bFGF stimulate the formation of new bone, increase osteoblast surface area, periosteal bone area and total bone area, both in the presence and absence of heparin. However, the increase in new bone under the calvaria (% new endosteal bone) effected by bFGF is inhibited by heparin (FIG. 3).

The time course of the bone changes following stimulation by 1 ug/injection of acidic FGF given with heparin was examined. The experimental design was as described above, except eight animals were injected for each time point. Four were injected with vehicle alone and four with FGF-1 and heparin. The mice were sacrificed on days 3, 7, 14, 21 and 36 and bone changes measured at two levels at least 200 um apart.

TABLE 3

| Time (Days) | Total Bone Area (mm$^2$) | New Bone Area % Original | Osteoblasts (% periosteal surface) | Prolif. Cell Width (µm) | Osteoclasts/ mm$^2$ Bone Area |
|---|---|---|---|---|---|
| aFGF | | | | | |
| 3 | 0.85 ± 0.04 | 2.0 ± 0.5 | 45 ± 10 | 23.7 ± 2.8$^a$ | 18 ± 3 |
| 7 | 1.06 ± 0.06 | 13.2 ± 2.9$^a$ | 78 ± 10 | 21.7 ± 3.1$^a$ | 12 ± 3 |
| 14 | 1.16 ± 0.03$^a$ | 32.1 ± 3.0$^a$ | 92 ± 4$^a$ | 15.5 ± 1.8$^a$ | 25 ± 6 |
| 21 | 1.40 ± 0.07$^a$ | 52.4 ± 7.9$^a$ | 90 ± 4$^a$ | 11.8 ± 2.1 | 22 ± 3 |
| 36 | 1.50 ± 0.12$^a$ | 64.1 ± 8.5$^a$ | 46 ± 16 | 10.9 ± 1.9 | 10 ± 5 |
| control | | | | | |
| 3 | 0.83 ± 0.06 | 0.1 ± 0.1 | 36 ± 11 | 5.7 ± 1.5 | 20 ± 7 |
| 7 | 0.88 ± 0.03 | 1.8 ± 0.4 | 35 ± 6 | 11 ± 2.1 | 18 ± 6 |
| 14 | 0.89 ± 0.06 | 3.6 ± 1.2 | 34 ± 13 | 4.0 ± 0.9 | 17 ± 5 |
| 21 | 0.95 ± 0.04 | 5.0 ± 1.9 | 29 ± 6 | 4.6 ± 0.6 | 7 ± 2 |
| 36 | 1.09 ± 0.06 | 10.5 ± 2.3 | 28 ± 7 | 2.8 ± 0.5 | 15 ± 5 |

$^a$Statistically different from control, $p < 0.01$

Figure 4:
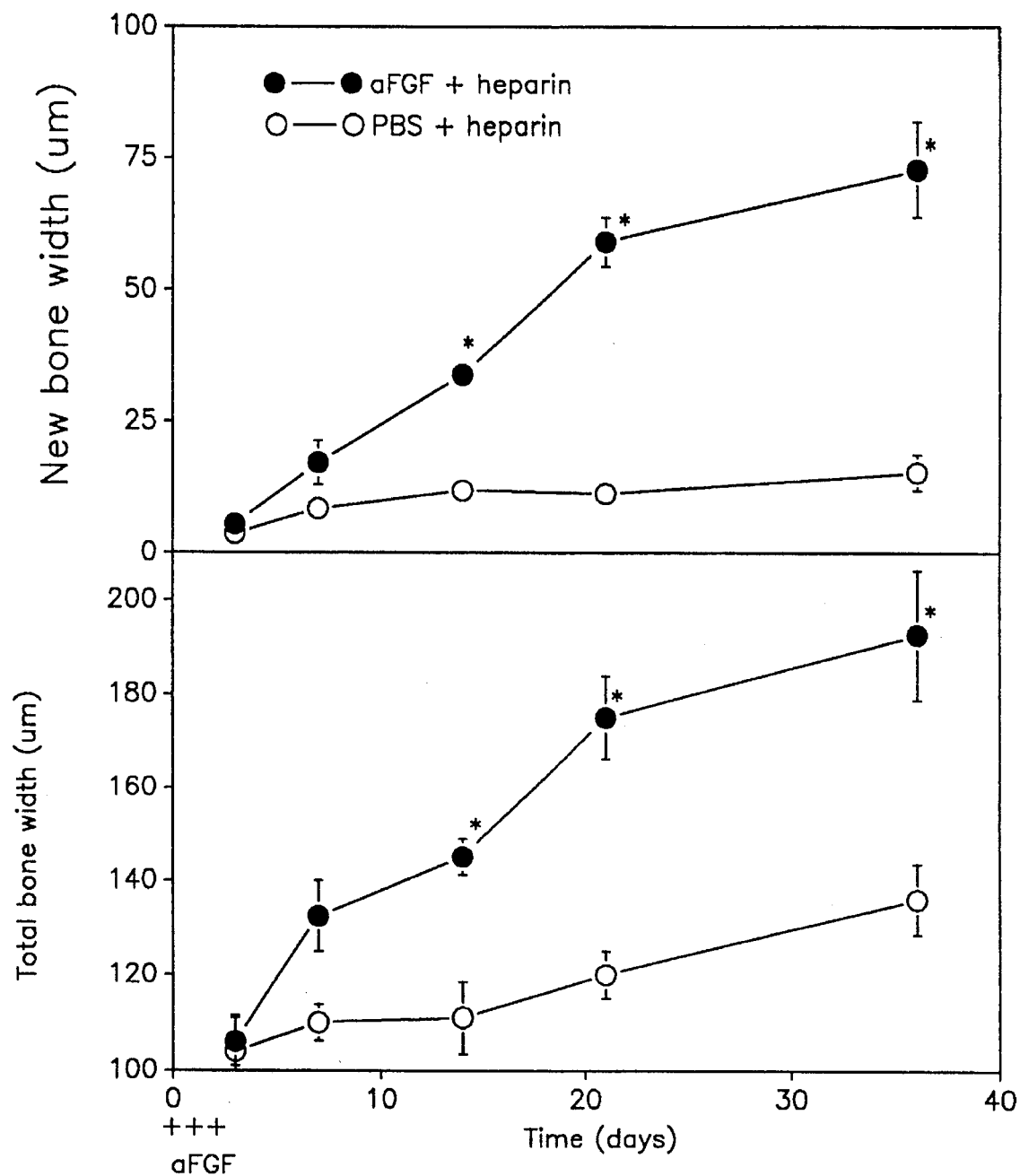
FIG. 4 demonstrates the time response of bone growth to aFGF.
Figure 5:
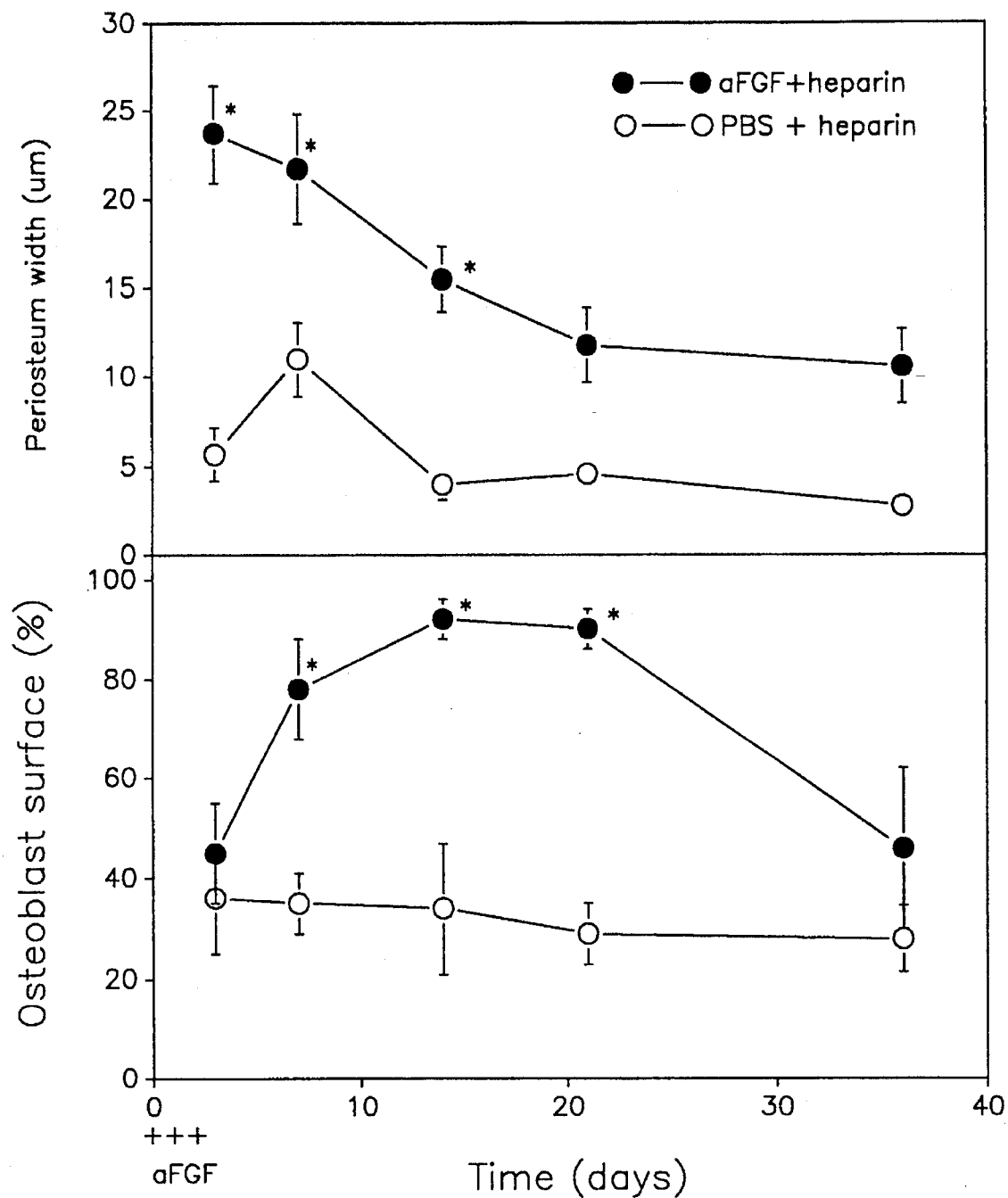
FIG. 5 demonstrates the time response of aFGF on periosteum proliferation and osteoblast differentiation to aFGF.

As can be seen on Table 3, FGF-1 produces a sustained stimulation of bone formation lasting 21 days after a three day pulse of treatment (FIG. 4). The initial response is one of cell proliferation, with differentiation of osteoblasts and matrix formation occurring only after the 3 days of treatment (FIG. 5). There is no evidence of enhanced osteoblast formation at any of the time periods examined.

The dose response of bone changes following four times daily stimulation by 0.5, 5.0, 50 and 500 ng/injection of FGF-1 or basic FGF given with and without heparin (50 U/ml) was also determined. Each treatment group comprised 4 Swiss ICR white male mice aged 4–6 weeks. Fourteen mice served as controls, 7 receiving vehicle alone (PBS+ 0.1% BSA) and 7 receiving vehicle and heparin.

Figure 6:
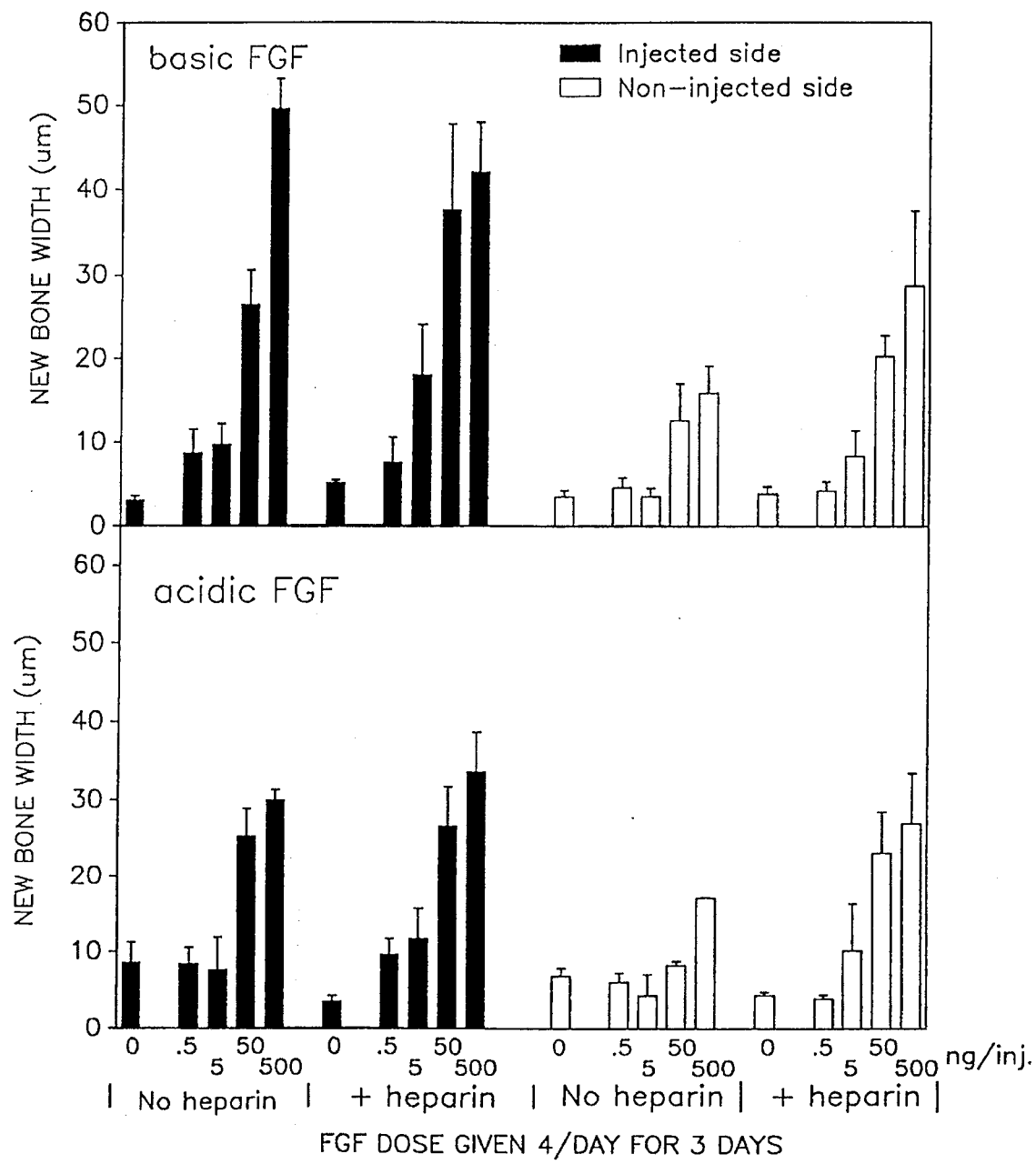
FIG. 6 demonstrates the dose response of the effects of aFGF and bFGF on bone formation of the calvaria.

The mice were sacrificed on day 14, and the calvaria prepared as described above. FIG. 6 demonstrates that both acidic FGF and basic FGF were active at the nanogram range in vivo. While bone responses were unchanged by heparin when administered alone, heparin enhanced the effects of both aFGF and bFGF particularly on the non-injected side of the calvaria.

FIG. 2 demonstrates that both FGF-1 and bFGF produced extensive formation of new woven bone on the upper periosteal surface that was rapidly mineralized. Basic FGF produced a maximum increase of greater than 100% in the thickness of the calvarium on the injected side and also induced new bone formation on the underside of the calvaria. Heparin increased the effect of aFGF. Neither aFGF or bFGF increased bone resorption or osteoblast number. In a study of time course and dose response, aFGF and heparin produced an initial vigorous but transient fibroblastic response. Osteoblast proliferation was apparent from day 3 to 21. By day 36, the osteoblast-lined upper periosteal surface had returned to normal and the most recently formed bone was clearly lamellar. The effects were dose dependent, with maximal response at 50 ng/injection.

EXAMPLE 5

In vivo Effects of Systemic Administration of FGF-1 in the Ovariectomized Rat

The ovariectomized rat is accepted as an animal model of human post-menopausal osteoporosis. To assess the effects of systemic administration of aFGF on skeletal tissues in an animal model of acute bone loss related to estrogen deficiency similar to that seen in post-menopausal women, female Sprague-Dawley rats (250 gms) were either sham-operated or surgically ovariectomized. Commencing seven days after surgery, rats were administered either vehicle (PBS), aFGF (0.2 mg/kg i.v. via tail vein) or estrogen (160 ug/kg s.c.) for 28 days. All injections were performed under methoxyflurane anesthesia. Prior to termination, all rats were administered single doses of tetracycline and demeclocycline to assess bone formation and mineralization. The tibias and lumbar vertebrae were removed, fixed, and processed, both decalcified and undecalcified, for histomorphometric evaluation.

Figure 7:
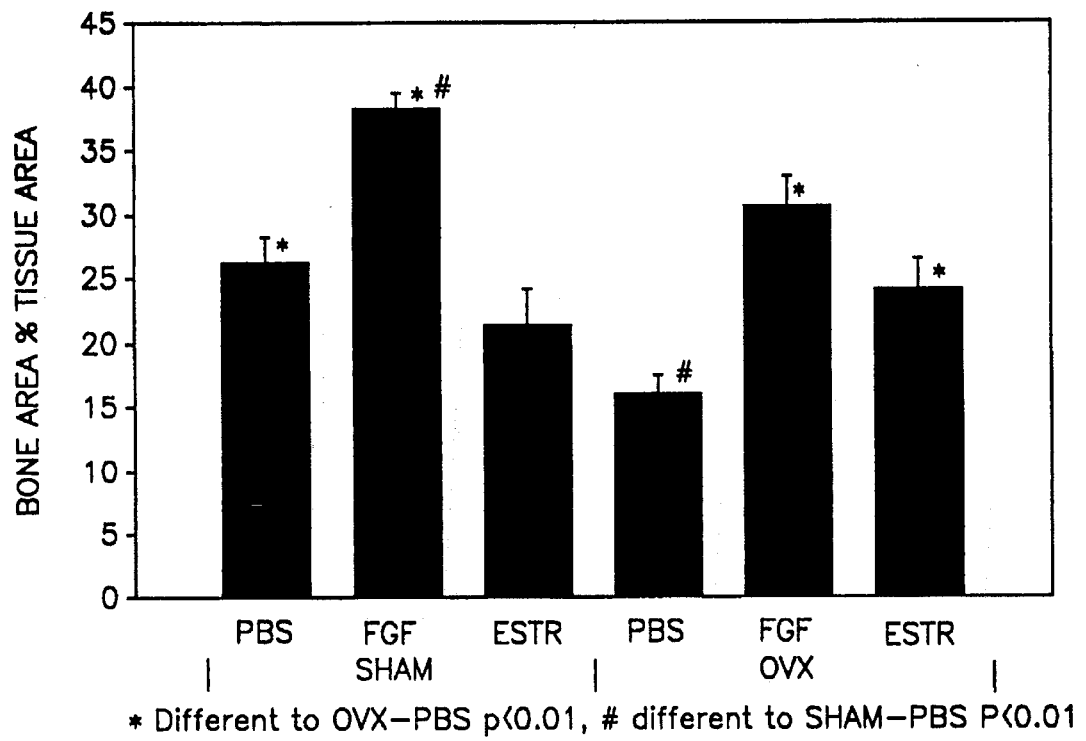
FIG. 7 demonstrates the effects of daily administration of aFGF on tibial bone loss in ovariectomized rats.
Figure 8:
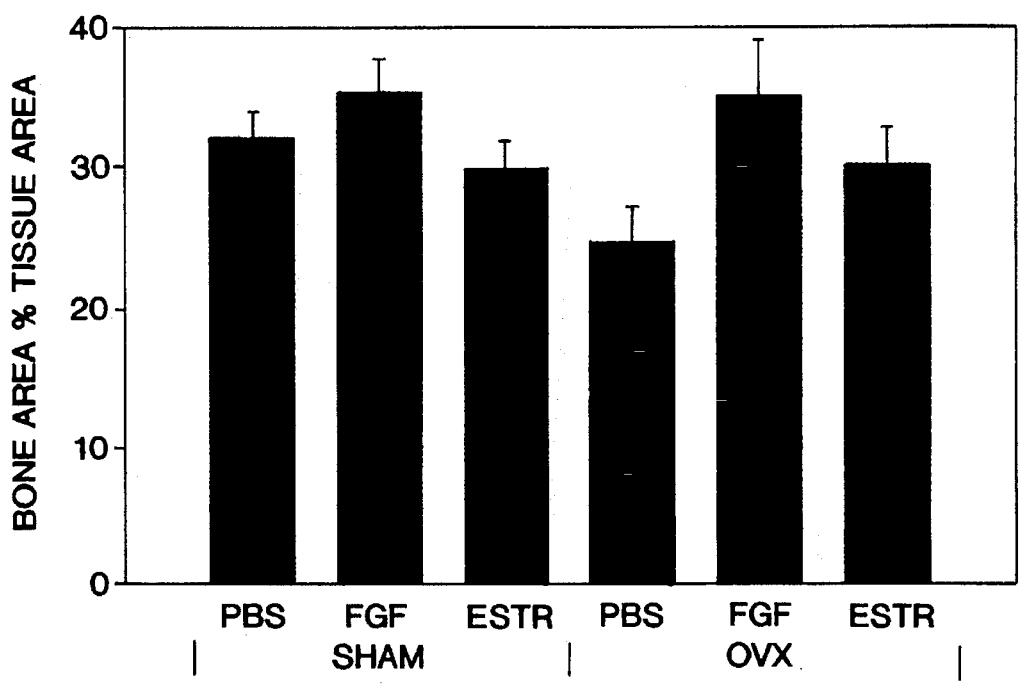
FIG. 8 demonstrates the effects of daily administration of aFGF on vertebral bone density in ovariectomized rats.

Cancellous bone area (expressed as a % of tissue area) was quantitated on decalcifed sections of tibial metaphysis and lumbar vertebrae. When compared with vehicle-treated ovariectomized rats, bone area in the region of the secondary spongiosa of the tibia was significantly increased in both sham-operated rats administered vehicle or aFGF and in ovariectomized rats administered FGF-1 or estrogen (FIG. 7). Similar but non-significant changes in cancellous bone area were observed in the lumbar vertebrae (FIG. 8). These data indicate that FGF-1 blocked the cancellous bone loss in the secondary spongiosa associated with estrogen deficiency. Additionally, periosteal bone formation was increased in FGF-1 treated sham-operated rats.

Figure 9:
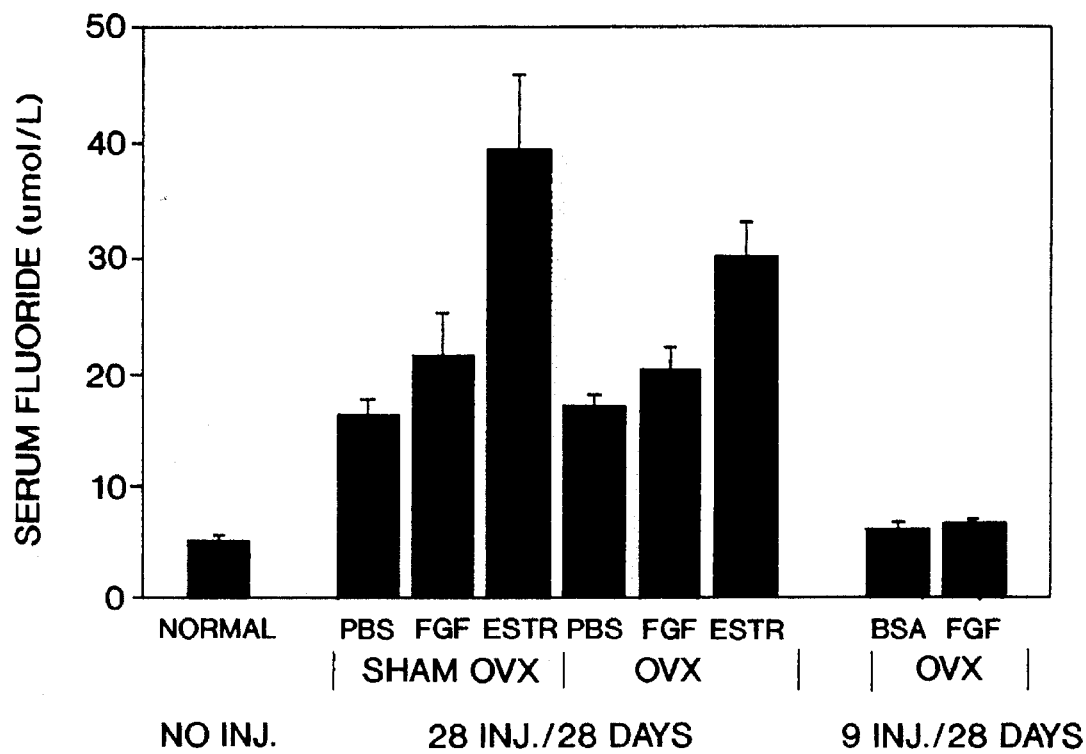
FIG. 9 demonstrates the levels of serum fluoride following methoxyflurane administration.

Qualitative assessment of sections of the tibia and vertebrae revealed that daily injection of aFGF induced new woven bone formation in the vertebrae, tibial diaphysis, and tibial epiphysis. Evaluation of undecalcified sections revealed that aFGF produced new bone which was poorly mineralized. This mineralization defect was likely a result of fluoride accumulation from the daily exposure to fluoride-containing gas anesthetic. This is supported by the increase in serum fluoride observed in these rats (FIG. 9).

To determine the response of the skeleton to cyclic administration of systemic FGF-1, 250 gm Sprague-Dawley rats were either sham-operated or surgically ovariectomized and were administered either vehicle or FGF-1 commencing 2 months post-surgery. Treatment was initiated 2 months following surgery because approximately 50% of the cancellous bone in the tibial metaphysis is lost in response to estrogen deficiency by this time. Rats were administered daily injections of either vehicle or FGF-1 (0.5 mg/kg/day i.v.) for three days followed by 6 days without treatment. This regimen was repeated 3 times. Rats were terminated on day 28. Prior to termination, rats were administered single doses of tetracycline and demeclocycline. Tibias, femurs, and lumbar vertebrae were removed for histomorphometric and dual energy X-ray absorptiometric analyses.

Figure 10:
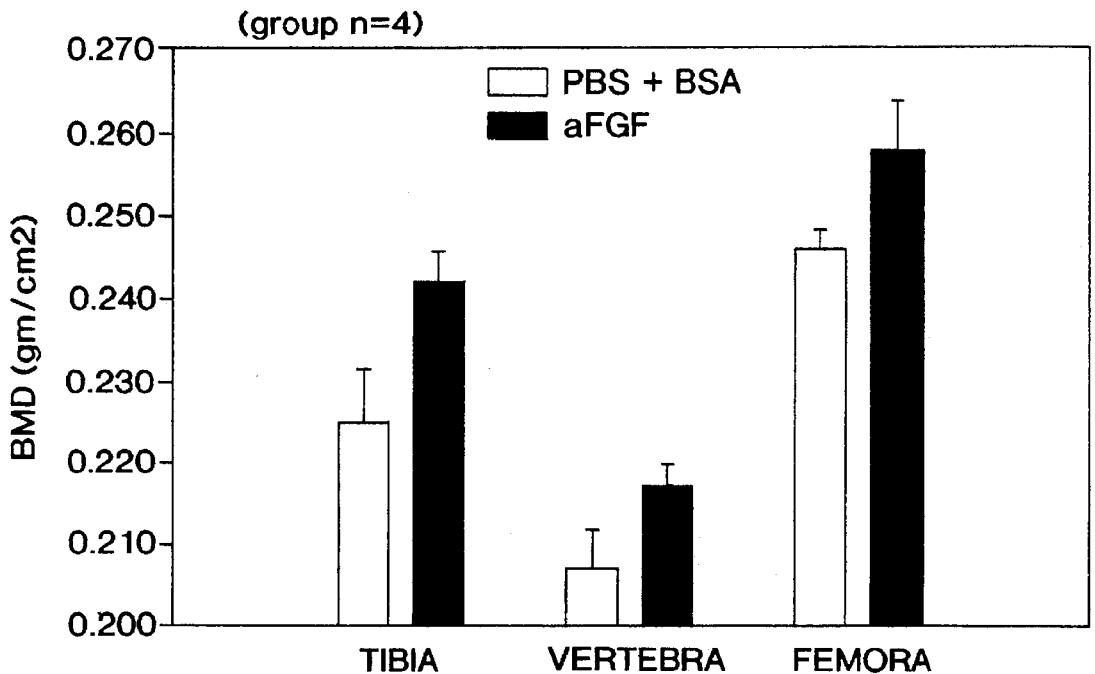
FIG. 10 demonstrates the effects of cyclic administration of aFGF on bone density in rats.
Figure 11:
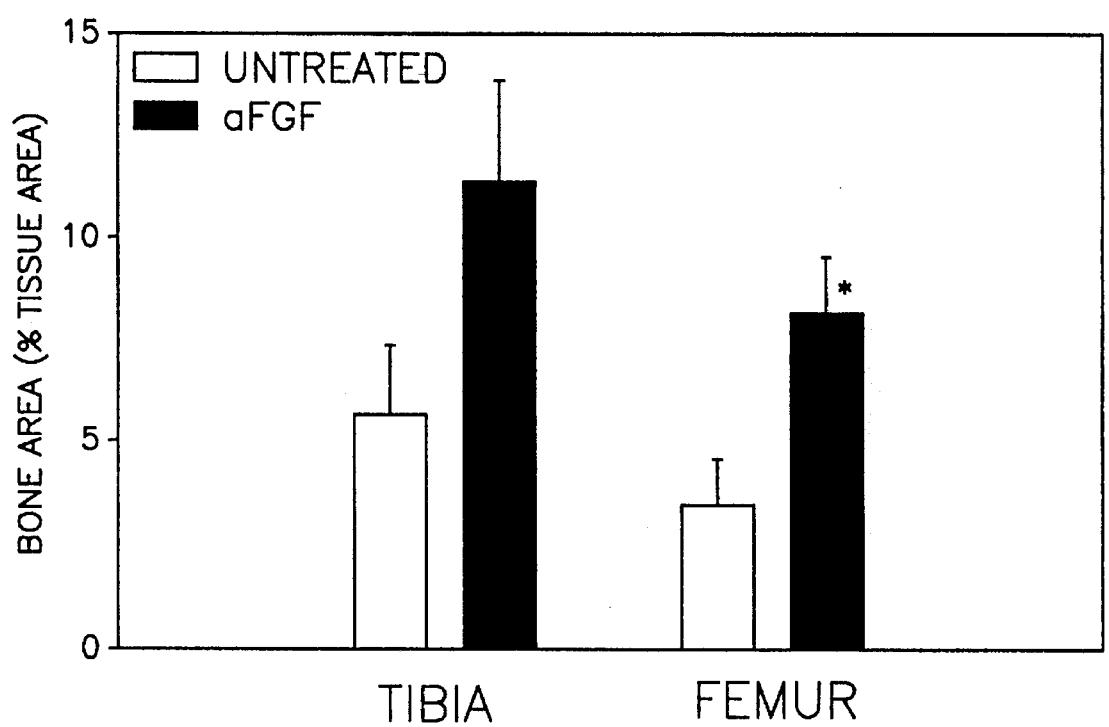
FIG. 11 demonstrates the effects of aFGF on bone mass in ovariectomized rats.

Bone mineral density (BMD), an assessment of bone mass, was determined with a Lunar DEXA. BMD was increased in the tibial metaphysis, lumbar vertebrae, and femur of the aFGF-treated rats compared with the vehicle treated group (FIG. 10). These data were corroborated by increases in cancellous bone area as determined by histomorphometic analysis in the tibial and femoral metaphyses in the FGF-1-treated rats (FIG. 11 ). Qualitative assessment revealed that cyclic systemic administration of FGF-1 induced some woven bone formation in the long bone shafts but not in the vertebrae or tibial epiphysis. Evaluation of the tetracycline labelling revealed that the new bone formed in response to aFGF was mineralized normally. Serum fluoride was not elevated in these rats. These data indicate that aFGF can maintain and increase bone mass in a model with established and progressive osteopenia.

EXAMPLE 6

Effects of Systemic FGF-1 Administration in the Aged Ovariectomized Rat

Established post-menopausal osteoporosis is a disease characterized by reduced cancellous and cortical bone mass, low bone turnover, and reduced connectivity of vertebral cancellous bone. To assess the potential effects of FGF-1 on these alterations, FGF-1 is administered systemically for 28 days to aged ovariectomized rats, an animal model of established cortical and cancellous osteopenia, low bone turnover, and reduced connectivity of vertebral cancellous bone. Eight 10-month old retired breeder Sprague-Dawley rats were either sham-operated or surgically ovariectomized. Six months following surgery, either vehicle or FGF-1 (0.2 mg/kg/day i.v.) was administered to ovariectomized rats. Sham-operated rats received vehicle alone. All injections were performed under isoflurane anesthesia. Half of the rats in each treatment group were terminated after 28 days of treatment. The remaining half is maintained an additional 28 days without treatment to determine the long-term consequences of FGF-1 treatment. Prior to termination, all rats received 2 injections of calcein green as a timed-tissue marker in bone to calculate bone formation rates. Femurs, tibias, and lumbar vertebrae were removed for DEXA and histomorphometric analysis as described above in Example 5. To perform biomechanical analyses, isolated lumbar vertebrae are compressed in a material testing machine at a constant compression rate to failure. Failure is designated as the point when the load deformation curve decreases after achieving maximal compressive strength.

DEXA analysis revealed that FGF-1 treatment caused a small but not significant increase in bone mineral density in femur, tibia and vertebrae at day 28. In the long bones, this increase is evident in the diaphyssis and metaphysis, indicating an increase in both cortical and cancellous bone. Vertebral cancellous bone connectivity is likely to be increased in the FGF-1-treated rats at day 28 and 56. These changes will translate into an increase in vertebral compressive strength in the vertebrae from the FGF-1-treated rats. These data indicate that systemic administration of FGF-1 increased both cortical and cancellous bone mass and increases vertebral cancellous bone connectivity and strength in and animal model of established post-menopausal osteoporosis.

One skilled in the art will readily appreciate the present invention is well adapted to carry out the objects and obtain the ends and advantages mentioned, as well as those inherent therein. The peptides, antibodies, methods, procedures and techniques described herein are presented as representative of the preferred embodiments, or intended to be exemplary and not intended as limitations on the scope of the present invention. Changes therein and other uses will occur to those of skill in the art that are encompassed within the spirit of the invention or defined by the scope of the appended claims.

---

What is claimed as new and intended to be covered by Letters Patent of the United States is:

1. A method of preventing or treating a pathological condition involving bone tissue in a human suffering therefrom comprising administering thereto an amount of human fibroblast growth factor effective to stimulate periosteal bone growth.

2. The method of claim 1 wherein said fibroblast growth factor is FGF-1.

3. The method of claim 2 wherein said FGF-1 is selected from the group consisting of ECGF α, aFGF and ECGF β.

4. The method of claim 3 wherein said FGF-1 is ECGF α.

5. The method of claim 3 wherein said FGF-1 is ECGF β.

6. The method of claim 3 wherein said FGF-1 is full length FGF-1.

7. The method of claim 1 wherein said pathological condition involving bone tissue is selected from the group consisting of osteoporosis, Paget's disease, periodontal disease, fractures and bone defects.

8. The method of claim 7 wherein said fibroblast growth factor is FGF-1.

9. The method of claim 7 wherein said pathological condition involving bone tissue is a fracture.

10. The method of claim 9 wherein said fibroblast growth factor is FGF-1.

11. The method of claim 10 further comprising administration of heparin or heparin fragments.

12. The method of claim 1 further comprising administration of heparin or heparin fragments.

13. The method of claim 12 wherein said fibroblast growth factor is FGF-1.

14. A method of treating osteoporosis in a human comprising administering to an individual in need of said treatment an amount of FGF-1 effective to stimulate periosteal bone growth.

15. The method of claim 14 further comprising administration of heparin or heparin fragments.

16. A method of treating dental pathological conditions in a human comprising administering locally at a site of the dental pathological condition to an individual in need of said treatment an amount of FGF-1 effective to stimulate periosteal bone growth.

17. The method of claim 16 further comprising administration of heparin or heparin fragments.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

Gly Ser Arg Pro Gly Ala Gly Thr
 1                  5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO (v) FRAGMENT TYPE: N-terminal (xi) SEQUENCE DESCRIPTION: SEQ ID NO:2:

Met Ala Ala Gly Ser Ile Thr
1                 5